United States Patent [19]

Nikles

[11] Patent Number: 4,528,374

[45] Date of Patent: Jul. 9, 1985

[54] POLYALKYLPIPERIDINES

[75] Inventor: Erwin Nikles, Liestal, Switzerland

[73] Assignee: Ciba-Geigy Corporation, Ardsley, N.Y.

[21] Appl. No.: 319,352

[22] Filed: Nov. 9, 1981

Related U.S. Application Data

[62] Division of Ser. No. 109,733, Jan. 4, 1980, Pat. No. 4,315,859.

[30] Foreign Application Priority Data

Jan. 15, 1979 [CH] Switzerland .............................. 357/79

[51] Int. Cl.³ .................. C07D 211/56; C07D 401/12
[52] U.S. Cl. ...................... 546/186; 546/191;
546/205; 546/203; 546/223; 546/244
[58] Field of Search ............... 546/191, 186, 205, 203, 546/223, 244

[56] References Cited

U.S. PATENT DOCUMENTS 3,937,711 2/1976 Cook ............................... 260/293.86
4,104,248 8/1978 Cantatore ....................... 260/45.8 N
4,326,063 4/1982 Son ....................................... 546/191

FOREIGN PATENT DOCUMENTS

WO81/01706 6/1981 PCT Int'l Appl. .

Primary Examiner—John M. Ford
Attorney, Agent, or Firm—Harry Falber

[57] ABSTRACT

Novel oligomer or polymer polyamine-1,3,5-triazines containing at least one polyalkylpiperidine radical, for example that of the formula

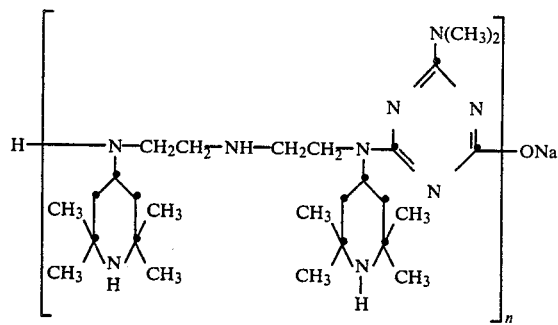

processes for their production, their use for stabilizing organic material, and the organic material protected therewith against oxidative and light-induced degradation.

2 Claims, No Drawings

POLYALKYLPIPERIDINES

This is a divisional of application Ser. No. 109,733 filed on Jan. 4, 1980, now U.S. Pat. No. 4,315,859.

The present invention relates to novel oligomer or polymer polyamine-1,3,5-triazines containing at least one polyalkylpiperidine radical, their manufacture, their use for stabilising organic material, and the organic material protected therewith against oxidative and light-induced degradation.

Polymer diamine-1,3,5-triazines containing polyalkylpiperidine radicals and their use for stabilising organic material are disclosed in German Offenlegungsschrift No. 2 636 144. It has been found, however, that a number of serious difficulties arise in the manufacture of these products, as insoluble by-products which are technically difficult to separate are formed.

It has now been found that it is possible to obtain polymer polyamine-1,3,5-triazines which have an excellent stabilising action without the above mentioned difficulties.

Accordingly, the present invention relates to novel polyamine-1,3,5-triazines of the general formula I

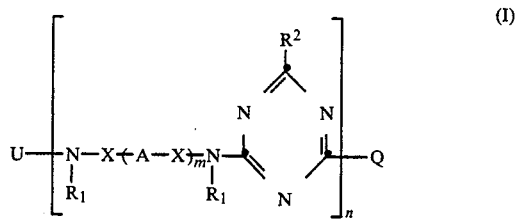   (I)

wherein the symbols which may or may not recur in the compound, and which on each possible recurrence can be the same or different, are defined as follows: X is $C_2$–$C_6$alkylene, A is —O—, —S— or —NR—, wherein R, which is also recurring or non-recurring and on each possible recurrence can be the same or different, is hydrogen, $C_1$–$C_{23}$alkyl which can be interrupted by oxygen, $C_3$–$C_{12}$cycloalkyl, $C_7$–$C_{18}$aralkyl, $C_6$–$C_{10}$aryl or the radical of the formula II

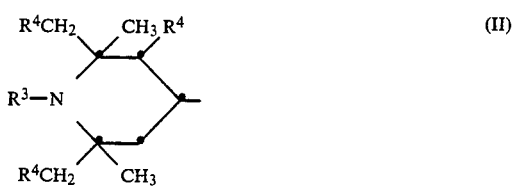   (II)

wherein $R^3$ is hydrogen, $C_1$–$C_{18}$alkyl, $C_3$–$C_{12}$alkenyl, $C_3$–$C_5$alkynyl, $C_3$–$C_{18}$alkoxyalkyl, $C_2$–$C_4$hydroxyalkyl which is unsubstituted or substituted by phenyl or phenoxy, or $C_7$–$C_{18}$aralkyl, and $R^4$ is hydrogen or methyl, or R is also one or more of the structural units contained with the brackets of formula I, said structural unit or units being terminally saturated by U and being bound through a triazine C-atom, and wherein R and $R^1$ as end groups, each independently of the other, can be hydrogen, $C_1$–$C_{23}$alkyl which can be interrupted by oxygen, $C_3$–$C_{12}$cycloalkyl, $C_7$–$C_{18}$aralkyl, $C_6$–$C_{10}$aryl or the radical of the formula II, and $R^1$ as end group can also in addition be a group of the formula III $$-(X-A)_p-X-NR^5R^6$$   (III)

wherein $R^5$ and $R^6$, each independently of the other, are U, $C_1$–$C_{23}$alkyl which can be interrepted by oxygen, $C_3$–$C_{12}$cycloalkyl, $C_7$–$C_{18}$aralkyl, $C_6$–$C_{10}$aryl or a radical of the formula II, and p is 0, 1, 2 or 3; m is 0, 1, 2, 3 or 4, $R^1$ can be hydrogen, $C_1$–$C_{23}$alkyl which can be interrupted by oxygen, $C_3$–$C_{12}$cycloalkyl, $C_7$–$C_{18}$aralkyl, $C_6$–$C_{10}$aryl, the radical of the formula II or a group of the formula IV, $$-(X-A)_p-X-N(R)_2$$   (IV)

$R^2$ is halogen cyano, azido, hydrazido, phenyl, —$OR^7$, —$SR^7$ or —$NR^8R^{8'}$, wherein $R^7$ is hydrogen, $C_1$–$C_{18}$alkyl, $C_3$–$C_{12}$alkenyl, $C_3$–$C_{18}$alkoxyalkyl, $C_3$–$C_{12}$cycloalkyl, $C_7$–$C_{18}$aralkyl, $C_6$–$C_{10}$aryl, or the radical of the formula II, and $R^8$ and $R^{8'}$, each independently of the other, are hydrogen, $C_1$–$C_{23}$alkyl which can be interrupted by oxygen, $C_3$–$C_{18}$alkenyl, $C_3$–$C_5$alkynyl, $C_2$–$C_{10}$hydroxyalkyl, $C_2$–$C_5$cyanoalkyl, $C_3$–$C_{12}$cycloalkyl, $C_7$–$C_{18}$aralkyl, $C_6$–$C_{10}$aryl or the radical of the formula II, or $R^8$ and $R^{8'}$ together with the nitrogen atom to which they are attached form a pyrrolidine ring or a piperidine, morpholine, or hexamethyleneimine ring which is unsubstituted or substituted by $C_1$–$C_4$alkyl, or $R^2$ on each of its possible recurrences can also be a radical of the formula V

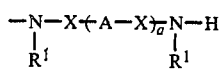   (V)

wherein a can be 0, 1, 2, 3 or 4, or a radical of the formula VI

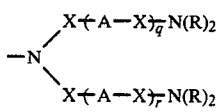   (VI)

wherein q can be 0, 1 or 2, and r can be 0, 1, 2 or 3, whilst the sum of r+q may not be more than 3, or $R^2$ can also be one or more of the structural units contained with the brackets of formula I, said structural unit or units being terminally saturated by Q and being bound through the amine nitrogen atom, and wherein $R^2$ as end group is halogen, phenyl, —$OR^7$, —$SR^7$, —$NR^8R^{8'}$, a group of the formula VII,

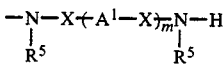   (VII)

or of the formula VIII

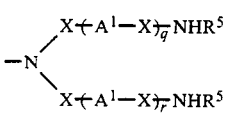   (VIII)

wherein $A^1$ is —O—, —S— or —$NR^5$, whilst Q is halogen, —$NR^8R^{8'}$, —OH, —OMe/b, wherein Me/b represents an alkali metal or alkaline earth metal of the valency, b, and b is 1 or 2, or Q is a radical of the formula VII or VIII, U is hydrogen, a group of the formula

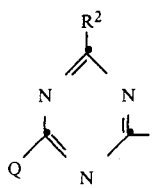

or $C_1$–$C_{24}$acyl, and n can be an integer from 1 to 100, with the proviso that at least one R, one $R^1$ or one $R^2$ is or contains a group of the formula II and, if m is 0, at least one $R^1$ must be a group of the formula III or IV.

$C_1$–$C_{18}$Alkyl can be methyl, ethyl, n-propyl, isopropyl, n-butyl, sec-butyl, n-pentyl, n-hexyl, n-octyl, 1,1,3,3-tetramethylbutyl, n-nonyl, decyl, dodecyl, tetradecyl, hexadecyl or octadecyl. Preferred alkyl groups are those containing 1 to 8 carbon atoms, especially those containing 1 to 4 carbon atoms.

$C_1$–$C_{23}$Alkyl radicals are the same as those defined above for $C_1$–$C_{18}$alkyl and are additionally e.g. nonadecyl, eicosyl, heneicosyl, docosyl and tricosyl. These hydrocarbon radicals can always be straight-chain or branched.

$C_1$–$C_4$Alkyl is methyl, ethyl, n-propyl, isopropyl, n-butyl, sec.butyl and tert-butyl.

$C_3$–$C_{12}$Cycloalkyl is for example cyclopropyl, cyclopentyl, cyclohexyl, cycloheptyl, cyclooctyl, cyclononyl or cyclododecyl. Cyclohexyl is preferred.

$C_7$–$C_{18}$Aralkyl is in particular 1-phenethyl, 1,1-dimethylbenzyl, 2-phenylethyl or, most preferably, benzyl.

$C_6$–$C_{10}$Aryl is for example phenyl which is substituted by methyl, ethyl, n-propyl, isopropyl, n-butyl, sec-butyl or tert-butyl. Unsubstituted phenyl groups are preferred.

$C_3$–$C_{18}$Alkenyl is in particular $C_3$–$C_{12}$alkenyl, for example allyl, methallyl, 2-butenyl, 2-hexenyl, 3-hexenyl, 2-octenyl, or 2-dodecenyl. Allyl is preferred.

$C_3$–$C_5$Alkynyl is for example propargyl, 1-butynyl, 2-butynyl or n-1-pentynyl. Propargyl is preferred.

The alkyl moiety of $C_3$–$C_{18}$alkoxyalkyl can contain 1 to 3 carbon atoms and the alkoxy moiety can contain 1 to 16 carbon atoms. Examples of $C_3$–$C_{18}$alkoxyalkyl are: ethoxymethyl, 2-methoxyethyl, 2-ethoxyethyl, 2-n-butoxyethyl, 3-n-butoxyethyl, 2-octoxyethyl or 2-hexadecyloxyethyl. Alkoxyalkyl groups containing 3 or 4 carbon atoms are preferred, for example ethoxymethyl, 2-methoxyethyl or 2-ethoxyethyl.

$C_2$–$C_{10}$Hydroxyalkyl is in particular $C_2$–$C_4$hydroxyalkyl, e.g. 2-hydroxy-n-butyl, 2-hydroxy-n-propyl, and, in particular, 2-hydroxyethyl.

Halogen is e.g. fluorine or, in particular, chlorine. $R^7$ and $R^8$ as $C_2$–$C_5$cyanoalkyl are in particular cyanoethyl.

X as $C_2$–$C_6$alkylene is e.g. ethylene, propylene, tetramethylene, pentamethylene and hexamethylene. Ethylene and propylene are preferred.

Me as alkali metal or alkaline earth metal is in particular Na, K, Li, Mg, Ca, Sr or Ba. Na, K and Ca are preferred.

U as $C_1$–$C_{24}$acyl is preferably $C_2$–$C_8$acyl and especially acetyl, propionyl, butyryl or benzoyl. U can also advantageously be formyl.

Particularly interesting compounds are those of the formula I, wherein X represents ethylene or propylene and A is —NR—, wherein R as recurring or non-recurring symbol, which can be different on each possible recurrence, is hydrogen, $C_1$–$C_8$alkyl, cyclohexyl, benzyl, the radical of the formula II, wherein $R^3$ is hydrogen, $C_1$–$C_{18}$alkyl, allyl, $C_2$–$C_4$hydroxyalkyl, benzyl, and $R^4$ is hydrogen, or R is one or more of the structural units contained within the bracket of formula I, said structural unit or units being terminally saturated by U and being bound through a triazine C-atom, wherein R and $R^1$ as end groups, each independently of the other, can be hydrogen, $C_1$–$C_8$alkyl, cyclohexyl, benzyl or the radical of the formula II as defined above, and $R^1$ as end group can also in addition be a group of the formula III, wherein $R^5$ and $R^6$, each independently of the other, can be U or the radical of the formula II as defined above, and p can be 0 or 1; $R^1$ as recurring or non-recurring symbol, which can be the same or different on each possible recurrence, is hydrogen or the radical of the formula II as defined above or a group of the formula IV, wherein A, X, R and p have the given meanings; m as recurring or non-recurring symbol, which can be the same or different on each possible recurrence, is 0, 1 or 2; $R^2$ as recurring or non-recurring symbol, which can be the same, or different on each possible recurrence, is chlorine, or —$NR^8R^{8'}$, wherein $R^7$ and $R^8$, each independently of the other, are hydrogen, $C_1$–$C_8$alkyl, allyl, $C_3$–$C_4$alkoxyalkyl, $C_2$–$C_4$hydroxyalkyl, cyclohexyl, benzyl or the radical of the formula II, wherein $R^3$ is hydrogen, $C_1$–$C_8$alkyl, allyl, $C_2$–$C_4$hydroxyalkyl, benzyl, and $R^4$ is hydrogen, or $R^2$ is also a radical of the formula V or VI, wherein A, X, R and $R^1$ have the given meanings, a is 1 or 2, q can be 0 and r can be 0 or 1, or $R^2$ can also be one or more of the structural units contained with the brackets of formula I, said structural unit or units being terminally saturated by Q and being bound through the amine nitrogen atom, and wherein $R^2$ as end group is chlorine or the group —$NR^8R^{8'}$ as define above or a group of the formula VII or VIII, wherein A' is —$NR^5$— and X, $R^5$, m and q have the given meanings Q; is chlorine, the group —$NR^7R^8$ as defined above, —OH, —OMe/b, wherein Me/b is an alkali metal or alkaline earth metal of the valency b, and b is 1 or 2, or Q is a radical of the formula VII or VIII as defined above; U is hydrogen, a group of the formula

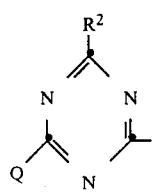

or acetyl, propionyl or benzoyl; and n can be an integer from 1 to 50, with the proviso that at least one R, one $R^1$ or one $R^2$ is and/or contains a group of the formula II, and, if m is 0, at least one $R^1$ must be a group of the formula III or IV.

Preferred compounds are those of the formula IX

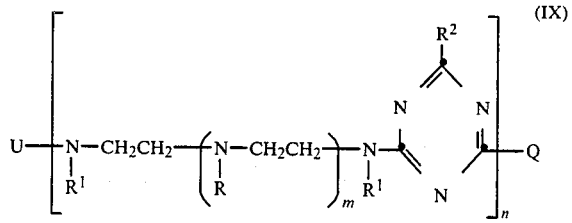

wherein m as recurring or non-recurring symbol, which can be the same or different on each possible recurrence, is 0, 1 or 2, R as recurring or non-recurring symbol, which can be the same or different on each possible recurrence, is hydrogen or one or more of the structural units contained within the bracket of formula I, said structural unit or units being terminally saturated by U and being bound through a triazine C-atom, and wherein R as end group is hydrogen and each $R^1$ as end group can independently be hydrogen, a group of the formula X

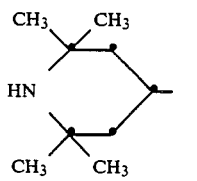

and $R^1$ as end group can also in addition be a group of the formula XI

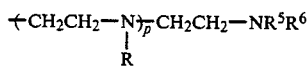

wherein $R^5$ is hydrogen and $R^6$ is a group of the formula X and p is 0 or 1, $R^1$ as recurring or non-recurring symbol, which can be the same or different on each possible recurrence, is hydrogen, a group of the formula X and, if m is 0, at least one $R^1$ is a group of the formula XII

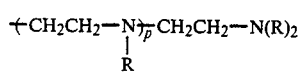

wherein R and p have the given meanings, $R^2$ as recurring or non-recurring symbol, which can be the same or different on each possible recurrence, is chlorine or $-NR^8R^{8'}$, wherein $R^8$ and $R^{8'}$, each independently of the other, are hydrogen, $C_1$-$C_8$alkyl, allyl, methoxyethyl, methoxypropyl, $C_2$-$C_4$hydroxyalkyl, cyclohexyl, benzyl, or a group of the formula X; Q is chlorine, the group $-NR^8R^{8'}$ as defined above, $-OH$, $-OMe/b$, wherein Me/b is an alkali metal or alkaline earth metal of the valency b and b is 1 or 2; U has the preferred meaning given above, and n can be an integer from 1 to 50, with the proviso that at least one R, one $R^1$ or one $R^2$ is and/or contains a group of the formula X.

Particularly preferred compounds are those of the formula IX, wherein $R^2$ is a group $-NR^8R^{8'}$, in which $R^8$ is hydrogen and $R^{8'}$ is $C_1$-$C_8$alkyl, cyclohexyl or a group of the formula X.

A further embodiment of the invention concerns a process for the production of the novel polymer polyamine-1,3,5-triazines. These compounds can be obtained by methods analogous to known ones by reacting a halogeno-1,3,5-triazine of the formula

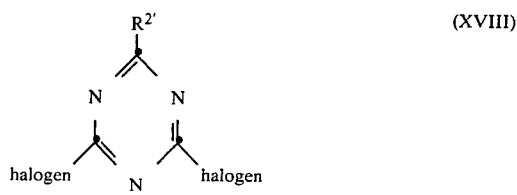

wherein $R^{2'}$ is halogen, cyano, azido, hydrazido, phenyl, $-O-R^7$, $-SR^7$ or $-NR^8R^{8'}$, in which $R^7$ is hydrogen, $C_1$-$C_{18}$alkyl, $C_3$-$C_{12}$alkenyl, $C_3$-$C_{18}$alkoxyalkyl, $C_3$-$C_{12}$cycloalkyl, $C_7$-$C_{18}$aralkyl, $C_6$-$C_{10}$aryl or the radical of the formula II

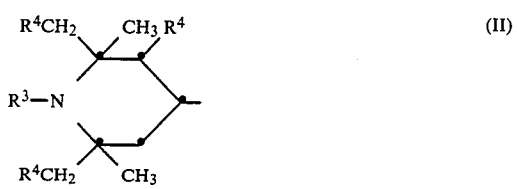

wherein $R^3$ is hydrogen, $C_1$-$C_{18}$alkyl, $C_3$-$C_{12}$alkenyl, $C_3$-$C_5$alkynyl, $C_3$-$C_{18}$alkoxyalkyl, $C_2$-$C_4$hydroxyalkyl which is unsubstituted or substituted by phenyl or phenoxy, or is $C_7$-$C_{18}$aralkyl, and $R^4$ is hydrogen or methyl, and each of $R^8$ and $R^{8'}$ independently is hydrogen, $C_1$-$C_{23}$alkyl which can be interrupted by oxygen, $C_3$-$C_{18}$alkenyl, $C_3$-$C_5$alkynyl, $C_2$-$C_{10}$hydroxyalkyl, $C_2$-$C_5$cyanoalkyl, $C_3$-$C_{12}$cycloalkyl, $C_7$-$C_{18}$aralkyl, $C_6$-$C_{10}$aryl or the radical of the formula II, or $R^8$ and $R^{8'}$ together with the nitrogen atom to which they are attached form a pyrrolidine ring or a piperidine, morpholine, or hexamethyleneimine ring which is unsubstituted or substituted by $C_1$-$C_4$alkyl, with a polyamine or a mixture of polyamines, or a mixture of at least 2 polyamines, of the formula

wherein X is $C_2$-$C_6$alkylene, A is $-O-$, $-S-$ or $-NR-$, each R independently is hydrogen, $C_1$-$C_{23}$alkyl which can be interrupted by oxygen, $C_3$-$C_{12}$cycloalkyl, $C_7$-$C_{18}$aralkyl, $C_6$-$C_{10}$aryl or the radical of the formula II, and c can be an integer from 1 to 4, with the proviso that at least one of $R^{2'}$ or R is or contains a group of the formula II, and, if desired, treating the compound so obtained with an acylating agent, such that, if a mixture of polyamines of the formula XIX is used, said mixture can contain an amount of an amine of the formula XIX in which c is 0, and whenever $R^{2''}$ is halogen, or if terminal halogen atoms are still present, the compound obtained can subsequently additionally be reacted with compounds of the formula XX

wherein $R^{2''}$ has the same meaning as $R^{2'}$ excepting halogen and phenyl.

The above compounds defined under formula I are products of this process. Halogen is preferably chlorine.

If the product is acylated after completion of the reaction, the acylation is carried out by methods which are known per se. Suitable acylating agents are carboxylic acids containing 1 to 24, preferably 2 to 8, carbon atoms, or halides or anhydrides thereof, e.g. acetic acid, acetyl chloride, acetic anhydride, propionic anhydride, butyryl chloride or benzoyl chloride.

A preferred embodiment of the process comprises reacting cyanuric chloride with a polyamine or a mixture of polyamines, or a mixture of at least 2 polyamines, of the formula XIX, wherein X, A and R are as defined above and c can be 1 or 2, such that, if a mixture of polyamines is used, said mixture can contain an amount of an amine of the formula XIX in which c is 0, and subsequently reacting the product obtained with compounds of the formula XX, wherein $R^{2''}$ is $-OR^7$, $-SR^7$ or $-NR^8R^{8'}$, and $R^7$, $R^8$ and $R^{8'}$ are as defined above, and, if desired, thereafter acylating the reaction product with an acylating agent, with the proviso that at least one of $R^{2''}$ or R is or contains a group of the formula II as defined above. The subsequent acylation constitutes a preferred embodiment.

A particularly preferred embodiment of the process comprises the use of a homogeneous polyamine of the formula XIX, wherein c can be 1 or 2.

If there is used a mixture of polyamines of the formula XIX containing an amount of an amine of the formula XIX in which c is 0, then said amount preferably does not exceed 50% by weight of the mixture of polyamines.

Halogeno-1,3,5-triazines of the formula XVIII, wherein $R^{2'}$ is as defined above with the exception of halogen and phenyl, can be obtained by reacting a cyanuric halide, preferably cyanuric chloride, with 1 mole of a compound of the formula XX. Halogeno-1,3,5-triazines of the formula XVIII, wherein $R^{2'}$ is phenyl, can be produced by methods analogous to the procedure described in Example 14.

The reaction of the halotriazines with the compounds of the formula XIX or with the compounds of the formula XX is carried out either in aqueous suspension or in the presence of an inert solvent, such as acetone, dioxane, toluene, or xylene, in a temperature range between −10° C. and the boiling temperature of the solvent. The reaction takes place in the presence of organic or inorganic bases in order to bind the hydrogen halide. Examples of preferred bases are triethylamine or tributylamine, sodium hydroxide, sodium carbonate or sodium bicarbonate, potassium hydroxide or potassium carbonate or calcium carbonate.

Polyamines of the formula XIX, wherein at least one R is a group of the formula II are obtained by methods which are known per se by reacting a polyamine of the formula XXI

   (XXI)

wherein X has the above meaning and c can be an integer from 1 to 4, with a ketone of the formula XXII

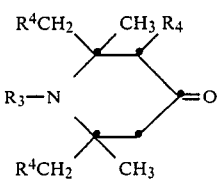   (XXII)

wherein $R^3$ and $R^4$ are as defined above, by means of catalytic hydrogenation.

The polyamines of the formula XIX, wherein c can be an integer from 1 to 4 and at least one R is a group of the formula II, and otherwise all the symbols have the general and preferred meanings assigned to them at the outset, are novel and can be used as intermediates and also as stabilisers in the same way as the end product of the formula I. They can also be used as hardeners for epoxy resins in the same way as the end products of the formula I.

The molar ratio of compounds of the formula XXI to compounds of the formula XXII can vary from 1:1 to 1:5, preferably from 1:1 to 1:2.

The molar ratio of cyanuric halides or of halotriazines of the formula XVIII to polyamines of the formula XIX depends on the ratio of the reactive groups.

A preferred embodiment is the two-step reaction of cyanuric chloride with a polyamine of the formula XIX, wherein at least one R is a group of the formula II, in the ratio of 0.8–1.2:1.2–0.8, whilst retaining a chloride atom at the triazine ring, and the subsequent reaction with an excess of an amine of the formula $HNR^8R^{8'}$.

The starting compounds are generally known and can be obtained by methods which are known per se.

The polymer triazines of the present invention can be used according to the present invention for stabilising plastics against damage by the action of oxygen, heat and light. Examples of such plastics are the polymers listed on pages 12 to 14 German Offenlegungsschrift No. 2,456,864.

A particularly important utility is the stabilising of polyolefins, styrene polymers and polyurethanes, for which the compounds of the invention are exceptionally suitable.

Examples of such materials which can be stabilised by the compounds of the formula I are polyethylene of high and lower density, polypropylene, especially also in the form of filaments, ribbons and sheets, ethylene/propylene copolymers, polystyrene, styrene/butadiene/acrylonitrile copolymers, mixtures of polyolefins or of styrene polymers, polyurethanes based on polyethers or polyesters in the form of films, filaments, lacquers, elastomers or foams. The compounds of the formula I are particularly suitable for stabilising ABS.

The stabilisers are added to the plastics in a concentration of 0.01 to 5% by weight, based on the weight of the material to be stabilised. Preferably, 0.03 to 1.5, most preferably 0.2 to 0.6% by weight of the compounds, based on the weight of the material to be stabilised, are incorporated therein.

The incorporation can be effected after the polymerisation, for example by blending the compounds and, if desired, further additives, into the melt by the methods conventionally employed in the art, before or during forming, or also by applying the dissolved or dispersed compounds to the polymers, if desired with subsequent evaporation of the solvent.

The novel compounds can also be added to the plastics to be stabilised in the form of a master batch which contains the compounds, for example in a concentration of 2.5 to 25% by weight. In the case of crosslinked polyethylene, the compounds are added before the crosslinking.

Accordingly, the invention also relates to the plastics stabilised by the addition of 0.01 to 5% by weight of a compound of the formula I and which can, if desired, also contain other known and conventional additives. The stabilised plastics can be used in a very wide variety of forms, for example as sheets, filaments, ribbons, profiles or as binders for lacquers, adhesives or cements.

Examples of further additives with which the stabilisers of the invention can be used, are: antioxidants, such as 2,6-dialkylphenols, derivatives of alkylated hydroquinones, hydroxylated thiodiphenyl ethers, alkylidene bisphenols, O-, N- and S-benzyl compounds, hydroxybenzylated malonates, hydroxybenzyl aromatics, s-triazine compounds, amides of $\beta$-(3,5-di-tert-butyl-4-hydroxyphenyl)-propionic acid, esters of $\beta$-(3,5-di-tert-butyl-4-hydroxyphenyl)-propionic acid, esters of $\beta$-(5-tert-butyl-4-hydroxyphenylacetic acid, acylaminophenols, benzylphosphonates, aminoaryl derivatives, UV absorbers and light stabilisers, such as 2-(2'-hydroxyphenyl)-benztriazoles, 2,4-bis-(2'-hydroxyphenyl)-6-alkyl s-triazines, 2-hydroxybenzophenones, 1,3-bis-2-(2'-hydroxybenzoly)-benzenes, esters of substituted or unsubstituted benzoic acids, acrylates, nickel compounds, sterically hindered amines, oxalic acid diamides, metal deactivators, phosphites, compounds which decompose peroxide, polyamide stabilisers, basic co-stabilisers, PVC stabilisers, nucleination agents or other additives, for example plasticisers, lubricants, emulsifiers, fillers, carbon black, asbestos, kaolin, talc, glass fibres, pigments, fluorescent whitening agents, flame retardants, antistatic agents.

Examples of further additives with which the stabilisers of the present invention can be used are listed on pages 18–24 of German Offenlegungsschrift No. 2,427,853.

The following Examples describe in more detail the manufacture and use of the compounds of the present invention.

EXAMPLE 1

100 g of triacetone amine and 36.5 g of diethylene triamine are dissolved in 1.4 liters of methanol. To this solution are added 1.5 g of conc. sulfuric acid and the reaction mixture is hydrogenated under normal pressure at 20° C. to 25° C. in the presence of 5 g of 5% platinum on carbon. The uptake of hydrogen is complete after 4 hours (15.4 liters; 0° C.; 760 mm Hg).

The catalyst is filtered off, the solvent evaporated and the residue distilled in a high vacuum. Boiling point: 161° C./0.08 mm Hg. Yield: 92 g of 1,7-bis-(2,2,6,6-tetramethyl-4-piperidyl)-1,4,7-triazaheptane in the form of a slightly yellow liquid.

19 g of 1,7-bis-(2,2,6,6-tetramethyl-4-piperidyl)-1,4,7-triazaheptane are dissolved in 200 ml of toluene. With stirring, a solution of 9.2 g of cyanuric chloride in 50 ml of toluene is added to the above solution, followed by the addition of 6.6 g of finely powdered sodium hydroxide. The mixture is stirred for 1 hour at 0° to 5° C. and for 1 hour at 40° C. and then refluxed for 16 hours. After cooling, the insoluble constituents are filtered off and the toluene solution is concentrated. The residue (16 g) is separated into two portions by crystallisation from 200 ml of hexane, affording crystals with a melting point of >260° C. and an average molecular weight $\overline{M}_n$ of 8100. The mother liquor is evaporated. Melting point: >260° C., $\overline{M}_n$: 2640.

EXAMPLE 2

The procedure of Example 1 is repeated, except that cyanuric chloride is reacted with 1,7-bis(2,2,6,6-tetramethyl-4-piperidyl)-1,4,7-triazaheptane in different molar ratios:

| | Molar ratio of cyanuric chloride/ amine | Working up | Melting point in °C. | $\overline{M}_n$ | Analysis (%) | | | | |
|---|---|---|---|---|---|---|---|---|---|
| | | | | | C | H | N | O | Cl |
| a | 1:3 | crystallisation from acetone at −78° C. | 30–40° | 940 | 66.0 | 11.3 | 19.9 | 3.1 | <0.1 |
| b | 1:2* | crystallisation from hexane at −78° C. | 100–108° | 2120 | 63.7 | 10.5 | 20.6 | 4.3 | 0.8 |
| c | 1:1.5 | 2 fractions by crystallisation from hexane | 260 | 3970 | 62.8 | 10.0 | 21.9 | 3.1 | 2.3 |
| | | crystals from mother liquor | 138–186° | 2250 | 63.5 | 10.4 | 21.5 | 2.3 | 2.2 |
| d | 1:0.75 | crystallisation from acetone | 260 | 7800 | 59.6 | 8.4 | 22.9 | 1.3 | 7.3 |

| Molar ratio of cyanuric chloride/ amine | | Working up | Melting point in °C. | $\overline{M}_n$ | Analysis (%) | | | | |
|---|---|---|---|---|---|---|---|---|---|
| | | | | | C | H | N | O | Cl |
| e | 1:4 | crude product | resin | | | | | | |

*The $^{13}$C NMR spectrum shows that the partial structure

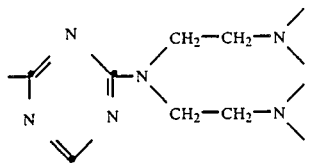

predominates over

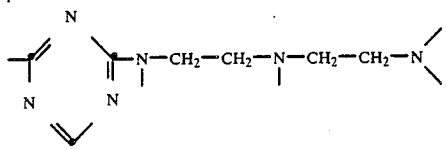

EXAMPLE 3

In analogy to the procedure of Example 1, 310 g of triacetone amine and 160 g of triethylenetetramine in 3 liters of methanol are hydrogenated in the presence of 2.5 g of conc. sulfuric acid and 15 g of 5% platinum on carbon. The resultant 1,10-bis(2,2,6,6-tetramethyl-4-piperidyl)-1,4,7,10-tetraazadecane boils at 182° C./0.01 mm Hg. 21.7 g of 1,10-bis(2,2,6,6-tetramethyl-4-piperidyl)-1,4,7-tetraazadecane are dissolved in 200 ml of toluene. With stirring, a solution of 9.1 g of 2-methylamino-4,6-dichlorotriazine in 100 ml of toluene is added to the above solution at 0° C. After addition of 4.5 g of finely powdered sodium hydroxide, the mixture is stirred at 0° to 5° C. for 1 hour, then for 1 hour at about 20° C., and finally for 16 hours under reflux. The insoluble constituents are filtered off, the filtrate is concentrated and the residue is crystallised from 200 ml of cyclohexane. Melting point: 130°–170° C., $\overline{M}_n$: 2700.

EXAMPLE 4

The following dichlorotriazines are reacted with 1,7-bis(2,2,6,6-tetramethyl-4-piperidyl)-1,4,7-triazaheptane in the molar ratio of 1:1 in a manner analogous to that described in Example 3.

Dichlorotriazine derivatives employed

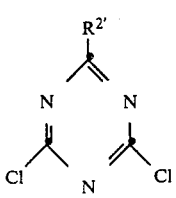

| | R$^{2'}$ | Working up | Melting point (°C.) | $\overline{M}_n$ |
|---|---|---|---|---|
| a | —OCH$_3$ | crystallisation from hexane | 142–163 | 1640 |
| b | —NH$_2$ | crystallisation from cyclohexane | 163–169 | 2140 |
| c | —NH(CH$_2$)$_3$OCH$_3$ | crude product | 69–83 | 1580 |
| d | —NH—C(CH$_3$)$_2$CH$_2$C(CH$_3$)$_3$ | crude product | 108–116 | 1530 |
| e | —NHCH$_2$—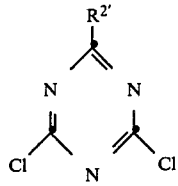 | crude product | 125–136 | 2280 |
| f | —NH—⟨H⟩ | crude product | 130–154 | 1760 |
| g | —N(CH$_3$)$_2$ | crude product | 73–86 | 1240 |
| h | —N(C$_4$H$_9$)$_2$ | crude product | resin | 1110 |
| i | —NH—⟨⟩ | crude product | resin | 3010 |

To saturate any terminal chlorine atoms still present, the products can be reacted with an excess of butylamine.

EXAMPLE 5

The 1,10-bis(2,2,6,6-tetramethyl-4-piperidyl)-1,4,7,10-tetraazadecane obtained in Example 3 is used as starting material.

25.6 g of 1,10-bis(2,2,6,6-tetramethyl-4-piperidyl)-1,4,7,10-tetraazadecane are dissolved in 200 ml of toluene. A solution of 5.5 g of cyanuric chloride in 50 ml of toluene is then added at 0° C. to the above solution in portions. Then 4 g of finely powdered sodium hydroxide are added. The mixture is stirred for 1 hour at 0° to 5° C., then for 1 hour at 40° C. and finally for 16 hours under reflux. The insoluble constituents are filtered off and the solution is concentrated. The residue is taken up in hexane, filtered once more and the product is precipitated by cooling with dry ice. Melting point: 100° to 120° C., $\overline{M}_n$: 2240.

EXAMPLE 6

Dichlorotriazine derivatives are reacted with 1,10-bis(2,2,6,6-tetramethyl-4-piperidyl)-1,4,7,10-tetraazadecane in the molar ratio 1:1 as described in Example 3. The crude products are either recrystallised or taken up in a solvent, filtered again and concentrated.

Dichlorotriazine derivatives employed $$\underset{Cl}{\overset{R^{2'}}{\underset{N}{\bigwedge}}}\underset{N}{\overset{N}{\bigwedge}}Cl$$

| | $R^{2'}$ | Working up | Melting point (°C.) | $\overline{M}_n$ |
|---|---|---|---|---|
| a | —OCH₃ | crystallisation from hexane | 53–75 | 1700 |
| b | —NH₂ | dissolve in methylene chloride, filter, | 142–151 | 2670 |
| c | —NHC(CH₃)₂CH₂C(CH₃)₃ | dissolve in hexane etc. | 103–118 | 1530 |
| d | —NH(CH₂)₃OCH₃ | dissolve in hexane etc. | 76–94 | 1820 |
| e | —NHCH₂—⌬ | dissolve in methylene chloride etc. | 88–112 | 2050 |
| f | —NH—⬡H | dissolve in methylene chloride etc. | 128–143 | 1750 |
| g | —N(CH₃)₂ | dissolve in hexane etc. | 110–135 | 1660 |
| h | —N(C₄H₉)₂ | dissolve in hexane etc. | 65–76 | 1700 |

EXAMPLE 7

A mixture of 155 g of triacetone amine, 113 g of diethylene triamine, and 2.5 g of conc. sulfuric acid in 2.5 liters of methanol is hydrogenated in the presence of 7 g of 5% palladium on carbon in the manner described in Example 1. In addition to yielding 1,7-bis(2,2,6,6-tetramethyl-4-piperidyl)-1,4,7-triazaheptane, distillation of the hydrogenation mixture yields at 115°–118° C./0.09 mm Hg 1-(2,2,6,6-tetramethyl-4-piperidyl)-1,4,7-triazaheptane as main product.

(a) 13.9 g of 2-(1,1,3,3-tetramethyl-1-butylamino)-4,6-dichloro-1,3,5-triazine are reacted with 12.1 g of 1-(2,2,6,6-tetramethyl-4-piperidyl)-1,4,7-triazaheptane in the presence of 5.4 g of powdered sodium hydroxide in the manner described in Example 1. The product is crystallised from hexane. Melting point: 156°–164° C., $\overline{M}_n$: 2020.

(b) 16.7 g of 2-(1,1,3,3-tetramethyl-1-butylamino)-4,6-dichlorotriazine are reacted with 9.7 g of 1-(2,2,6,6-tetramethyl-4-piperidyl)-1,4,7-triazaheptane (molar ratio 3:2) in the presence of 4.8 g of powdered sodium hydroxide. Recrystallisation from hexane yields a product with a melting point of 160°–196° C. $\overline{M}_n$: 2380, chlorine content: 3.3%.

The following dichlorotriazines are reacted with 1-(2,2,6,6-tetramethyl-4-piperidyl)-1,4,7-triazaheptane in analogous manner:

$$\underset{Cl}{\overset{R^{2'}}{\underset{N}{\bigwedge}}}\underset{N}{\overset{N}{\bigwedge}}Cl$$

| | $R^{2'}$ | molar ratio | m.p. (crude product) | $\overline{M}_n$ | Working up |
|---|---|---|---|---|---|
| c | —N(CH₃)₂ | 1:1 | 121–126° | 1595 | dissolve in acetone, filter |
| d | —N(C₄H₉)₂ | 1:1 | 92–96° | 1790 | dissolve in hexane, filter |
| e | —OCH₃ | 3:2 | >260 | 3170 | dissolve in methylene chloride, filter |

EXAMPLE 8

The following polyamines are obtained in a manner analogous to that described in Example 1:
(a) 1,9-bis(2,2,6,6-tetramethyl-4-piperidyl)-1,5,9-triazanonane (boiling point 183° C./0.5 mm Hg) from triacetone amine and dipropylene triamine;
(b) 1,9-bis(2,2,6,6-tetramethyl-4-piperidyl)-5-methyl-1,5,9-triazanonane (boiling point 200° C./0.5 mm Hg) from triacetone amine and bis-(3-aminopropyl)-methylamine;
(c) 1,17-bis-)2,2,6,6-tetramethyl-4-piperidyl)-1,5,9,13,17-pentaazaheptadecane (boiling point 200° C./0.001 mm Hg) from triacetone amine and tetrapropylene pentamine;
(d) 1,13-bis-(2,2,6,6-tetramethyl-4-piperidyl)-1,5,9,13-tetraazatridecane (boiling point 176° C./0.005 mm Hg) from triacetone amine and tripropylene tetramine;
(e) 1,14-bis-(2,2,6,6-tetramethyl-4-piperidyl)-1,14-diaza-5,10-dioxatetradecane (boiling point 173° C./0.001 mm Hg) from triacetone amine and 4,9-dioxadecane-1,12-diamine, in the presence of 78 g of 5% platinum on carbon;
(f) 1,9-bis(2,2,6,6-tetramethyl-4-piperidyl)-5-cyclohexyl-1,5,9-triazanonane from triacetoneamine and bis(3-aminopropyl)-cyclohexylamine;
(g) 1,9-bis(2,2,6,6-tetramethyl-4-piperidyl)-5-n-butyl-1,5,9-triazanonane from triacetoneamine and bis(3-aminopropyl)butylamine;
(h) 1,9-bis(2,2,6,6-tetramethyl-4-piperidyl)-5-octadecyl-1,5,9-triazanonane from triacetoneamine and bis(3-aminopropyl)-octadecylamine;

(i) 1,9-bis(2,2,6,6-tetramethyl-4-piperidyl)-5-cyclododecyl-1,5,9-triazanonane from triacetoneamine and bis(3-aminopropyl)-cyclododecylamine;

(k) 1,9-bis(2,2,6,6-tetramethyl-4-piperidyl)-5-benzyl-1,5,9-triazanonane from triacetoneamine and bis(3-aminopropyl)-benzylamine;

(l) 1,9-bis(2,2,6,6-tetramethyl-4-piperidyl)-5-phenyl-1,5,9-triazanonane from triacetoneamine and bis(3-aminopropyl)-aniline;

(m) 1,9-bis(2,2,6,6-tetramethyl-4-piperidyl)-1,9-diaza-5-oxa-nonane (b.p. 154° C./0.05 mm Hg) from triacetoneamine and bis(3-aminopropyl)ether;

(n) 1,9-bis(1,2,2,6,6-pentamethyl-4-piperidyl)-1,9-diaza-5-oxa-nonane from 1-methyl-triacetoneamine and bis(3-aminopropyl)ether;

(o) 1-isopropyl-7(2,2,6,6-tetramethyl-4-piperidyl)-1,4,7-triazaheptane (boiling point 115° C./0.05 mm Hg) from 1-(2,2,6,6-tetramethyl-4-piperidyl)-1,4,7-triazaheptane and acetone;

(p) 1-isobutyl-7(2,2,6,6-tetramethyl-4-piperidyl)-1,4,7-triazaheptane (boiling point 115° C./0.05 mm Hg) from 1-(2,2,6,6-tetramethyl-4-piperidyl)-1,4,7-triazaheptane and isobutyraldehyde;

(q) 1-cyclohexyl-7(2,2,6,6-tetramethyl-4-piperidyl)-1,4,7-triazaheptane (boiling point 151° C./0.05 mm Hg) from 1-(2,2,6,6-tetramethyl-4-piperidyl)-1,4,7-triazaheptane and cyclohexanone;

(r) mixture of 1-(1,2,2,6,6-pentamethyl-4-piperidyl)-1,4,7-triazaheptane and 1,7-bis(1,2,2,6,6-pentamethyl-4-piperidyl)-1,4,7-triazaheptane (boiling point 143°-162° C./0.2 mm Hg) from 1,2,2,6,6-pentamethyl-4-piperidone and diethylenetriamine;

(s) 1,7-bis(2,6-diethyl-2,3,6-trimethyl-4-piperidyl)-1,4,7-triazaheptane (b.p. 160° C./0.02 mm Hg) after repeated distillation in a molecular distillation apparatus) from 2,3,6-trimethyl-2,6-diethyl-4-piperidone and diethylenetriamine in the presence of 5% (based on the educts) of 5% platinum on carbon;

(t) 1-benzyl-7(2,2,6,6-tetramethyl-4-piperidyl)-1,4,7-triazaheptane (boiling point 172° C./0.4 mm Hg) from 1-(2,2,6,6-tetramethyl-4-piperidyl)-1,4,7-triazaheptane and benzaldehyde.

The above polyamines can be reacted with cyanuric acid derivatives to yield oligomer and polymer compounds by procedures analogous to those described in Examples 1, 3 or 9.

EXAMPLE 9

(a) With stirring, 46.1 g of cyanuric chloride in 1 liter of toluene are added dropwise at 0° C. to a solution of 95.4 g of 1,7-bis(2,2,6,6-tetramethyl-4-piperidyl)-1,4,7-triazaheptane in 2 liters of toluene. Then 500 ml of 1N sodium hydroxide solution are added in portions at the same temperature. The mixture is stirred initially for 1 hour at 0° C., then for 1 hour at room temperature, and finally for 2½ hours at 40° C. Titration with 0.1N hydrochloric acid in 2 ml of the aqueous phase reveals 0.042 m-equivalents of base.

The aqueous phase is separated and the toluene solution is washed twice with water and concentrated in vacuo at a maximum temperature of 40° C. The residue is taken up in chloroform, filtered clear, and concentrated at moderate temperature.

Yield: 100 g of a slightly yellowish product. Melting point: <260° C.; $\overline{M}_n$: 3150; chlorine content 7.23%. The polymer can be crystallised from hexane as a colourless product. Melting point: 256°–281° C.; $\overline{M}_n$: 4270; chlorine content: 6.98%.

Cyanuric chloride is reacted in the same way with polyamines in the molar ratio 1:1:

| | Polyamine | Product m.p. (°C.) | $\overline{M}_n$ |
|---|---|---|---|
| 1 | 1-cyclohexyl-7(2,2,6,6-tetramethyl-4-piperidyl)-1,4,7-triazaheptane | 156–170° | 3200 |
| 2 | 1,9-bis(2,2,6,6-tetramethyl-4-piperidyl)-1,9-diaza-5-oxanonane | 112–140° | 3600 |
| 3 | 1,7-bis(2,6-diethyl-2,3,6-trimethyl-4-piperidyl)-1,4,7-triazaheptane | 141–186° | 2311 |
| 4 | 1-isopropyl-7(2,2,6,6-tetramethyl-4-piperidyl)-1,4,7-triazaheptane | 124–143° | 4500 |
| 5 | 1,17-bis(2,2,6,6-tetramethyl-4-piperidyl)-1,5,9,13,17-pentaazaheptadecane | 87–119° | |
| 6 | 5-(2,2,6,6-tetramethyl-4-piperidyl)-1,5,9-triazanonane | | |
| 7 | mixture of 1,7-bis(1,2,2,6,6-pentamethyl-4-piperidyl)-1,4,7-triazaheptane (80%) and 1-(1,2,2,6,6-pentamethyl-4-piperidyl)-1,4,7-triazaheptane (20%) | 140° decomp. | |

(b) 30 ml of n-butylamine are added to 10 g of the crude product obtained from cyanuric chloride and 1,7-bis(2,2,6,6-tetramethyl-4-piperidyl)-1,4,7-triazaheptane and the mixture is refluxed for 16 hours. The solution obtained is diluted with 100 ml of methylene chloride, washed three times with 60 ml of 10% sodium carbonate solution, dried over anhydrous sodium sulfate, and concentrated. The residue is treated with acetonitrile. The insoluble solid is collected by filtration and dried in vacuo, affording 8.2 g of colourless product. Melting point: 156°–158° C.; $\overline{M}_n$: 3800; chlorine content: 0.1%. The product is readily soluble in methanol, chloroform, and toluene, soluble in hot hexane, and insoluble in acetonitrile.

The following amines can be reacted in exactly the same manner:

| | Amine | Product m.p. (°C.) | $\overline{M}_n$ |
|---|---|---|---|
| 1 | cyclopropylamine | 199–209° | 3300 |
| 2 | allylamine | 152–156° | 2970 |
| 3 | isobutylamine | 151–156° | 4100 |
| 4 | sec-butylamine | 169–172° | 3300 |
| 5 | diethylamine | 178–183° | 3700 |
| 6 | pyrrolidine | 196–203° | 3800 |
| 7 | piperidine | 240° | 2520 |
| 8 | morpholine | 210° | 4800 |

The following products obtained from cyanuric chloride with polyamines are reacted with butylamine in the same manner:

| | Polyamine | m.p. (°C.) | $\overline{M}_n$ |
|---|---|---|---|
| 9 | 1,9-bis(2,2,6,6-tetramethyl-4-piperidyl)-1,9-diaza-5-oxanonane | 144–165° | 3300 |
| 10 | 1,7-bis(2,6-diethyl-2,3,6-trimethyl-4-piperidyl)-1,4,7-triazaheptane | 99–113° | 2200 |
| 11 | 1,17-bis(2,2,6,6-tetramethyl-4-piperidyl)-1,5,9,13,17-pentaaza- | 98–111° | 4200 |

-continued

| Polyamine | m.p. (°C.) | $\overline{M}_n$ |
|---|---|---|
| heptadecane | | |

EXAMPLE 10

6 g of the crude polymer obtained in accordance with Example 9(a) from cyanuric chloride and 1,7-bis(2,2,6,6-tetramethyl-4-piperidyl)-1,4,7-triazaheptane are heated with 20 ml of 2-ethylhexylamine for 16 hours to 130° C. The reaction mixture is worked up as described in Example 9(b) for the reaction with n-butylamine, affording 5.3 g of a colourless product (m.p. 135°-138° C.; $\overline{M}_n$: 3600) which is readily soluble in acetone, chloroform and toluene at room temperature, but is soluble in hexane only at elevated temperature.

The following amines are reacted in the same manner:

| | Amine | Product m.p. (°C.) | $\overline{M}_n$ |
|---|---|---|---|
| a | n-hexylamine | 136–140° | 2190 |
| b | n-octylamine | 116–118° | 2300 |
| c | n-octydecylamine | 99–102° | 2300 |
| d | oleylamine | 60° | 2160 |
| e | β-hydroxyethylamine | 220–236° | 2900 |
| f | γ-methoxypropylamine | 157–160° | 4500 |
| g | cyclohexylamine | 186–190° | 2430 |
| h | benzylamine | 192–193° | 4300 |
| i | β-phenylethylamine | 157–162° | 4800 |
| k | norbornylamine | 236–253° | 2970 |
| l | dibutylamine | 162–166° | 6000 |
| m | 2,2,6,6-tetramethyl-4-piperidylamine | 241–256° | 4400 |

It is also possible to react the following amines in the same manner: 3,5,5-trimethylhexylamine, isotridecylamine, 3-isononyloxypropylamine, 3-stearyloxypropylamine, 3,3,5-trimethylcyclohexylamine, cyclododecylamine.

EXAMPLE 11

By a procedure analogous to that described in Example 9(a), cyanuric chloride is reacted with (a) 1,9-bis(2,2,6,6-tetramethyl-4-piperidyl)-1,5,9-triazanonane and (b) with 1,10-bis(2,2,6,6-tetramethyl-4-piperidyl)-1,4,7-tetraazadecane to produce polymers which still contain about one chlorine atom in each triazine ring.

(a) Melting point: 146°-154° C.; $\overline{M}_n$: 2640
(b) Melting point: 162°-166° C.; $\overline{M}_n$: 3270.

The further reaction with the N-alkylamines listed in the table below yields the following products:

| | | Polyamine | | | |
|---|---|---|---|---|---|
| | | 1,9-bis(2,2,6,6-tetramethyl-4-piperidyl)-1,5,9-triazanonane | | 1,10-bis(2,2,6,6-tetramethyl-4-piperidyl)-1,4,7,10-tetraazadecane | |
| | Amine | m.p. (°C.) | $\overline{M}_n$ | m.p. (°C.) | $\overline{M}_n$ |
| a | n-butylamine | 123–129° | 2590 | 142–145° | 5500 |
| b | n-hexylamine | 119–122° | 3000 | 137–142° | 5200 |
| c | n-octylamine | 81–84° | 2210 | 114–121° | 5800 |

EXAMPLE 12

96.4 g of 1,14-bis(2,2,6,6-tetramethyl-4-piperidyl)-1,14-diaza-5,10-dioxatetradecane, dissolved in 1 liter of toluene, is treated dropwise at 0° C. with 36.8 g of cyanuric chloride in 200 ml of toluene. Then 400 ml of 1N sodium hydroxide solution are added in portions and the mixture is stirred initially for 1 hour at 0° C. and then for 4 hours at 40° C. The mixture is filtered and the aqueous phase separated. The organic phase is concentrated at a maximum temperature of 90° C. in vacuo and the residue is taken up in methylene chloride. The methylene chloride solution is filtered and the solvent is removed by evaporation, yielding the product in the form of a soft, tacky resin. $\overline{M}_n$: 3045.

50 ml of n-butylamine are added to 15 g of the above product and the mixture is refluxed for 16 hours. The solution is diluted with methylene chloride, washed twice with dilute sodium carbonate solution and then with water, dried, and concentrated, affording as residue a product with a melting point of 66°-92° C. A product with a melting point of 60°-76° C. is obtained by reacting the above product with n-hexylamine.

EXAMPLE 13

In a manner analogous to that described in Example 9, 84.6 g of 5-methyl-1,9-bis(2,2,6,6-tetramethyl-4-piperidyl)-1,5,9-triazaheptane are reacted with 36.8 g of cyanuric chloride to produce a polymer ($\overline{M}_n$: 2900; m.p. 140°-176° C.).

This polymer is reacted with an excess of the following amines as described in Examples 9 and 10:

| | Amine | Product m.p. (°C.) | $\overline{M}_n$ |
|---|---|---|---|
| a | n-butylamine | 123–130° | 3000 |
| b | n-hexylamine | 111–115° | 2400 |
| c | n-octylamine | 92–97° | 3000 |
| c | n-octadecylamine | 62–68° | 2000 |

EXAMPLE 14

50 g of 2,4-dichloro-6-phenyltriazine, 84.4 g of 1,7-bis(2,2,6,6-tetramethyl-4-piperidyl)-1,4,7-triazaheptane, 17.7 g of finely powdered sodium hydroxide and 500 ml of toluene are refluxed for 16 hours. The mixture is filtered clear and the filtrate is concentrated. The residue melts at 136°-151° C.

EXAMPLE 15

6.6 g of the product melting at 60°-76° C. obtained in Example 12 are dissolved in 20 ml of methyl ethyl ketone. To the solution are added 3.5 g of finely powdered potassium carbonate and 0.2 g of potassium iodide, followed by the dropwise addition of 3.6 g of benzyl bromide at 80° C. The mixture is refluxed for 40 hours and, after the addition of 50 ml of methyl ethyl ketone, filtered. The filtrate is concentrated and the residue is dissolved in methylene chloride. The solution is washed with water and the solvent is removed by evaporation. The residue is triturated with acetonitrile and filtered. A benzylation product with a melting point of 73°-86° C. is obtained.

EXAMPLE 16

(a) 20 g of the crude polymer obtained in Example 9(a), 10 ml of ethylenediamine and 50 ml of toluene are refluxed for 16 hours. The mixture is washed with dilute sodium carbonate solution and then with water, dried over sodium sulfate, and concentrated. The residue is triturated with acetonitrile and filtered, affording a product with a melting point of 203°-206° C.; $\overline{M}_n$: 4700.

The above procedure is repeated, substituting 20 ml of hydrazine hydrate or 20 g of hexamethylenediamine for ethylenediamine. The physical data of the resultant products are as follows:

(b) with hydrazine hydrate: m.p. 210° C.; $\overline{M}_n$: 3800

(c) with hexamethylenediamine: m.p. 181° C.; $\overline{M}_n$: 4200.

EXAMPLE 17

14.8 g of the crude polymer obtained in Example 9(a) are dissolved in 100 ml of toluene and to the solution are added 7 g of dodecylmercaptan, 35 ml of 1N sodium hydroxide solution and 65 ml of water. The mixture is stirred for 24 hours at room temperature while introducing an excess of triethylamine gas in the course of the first 8 hours. The toluene phase is separated, washed twice with sodium hydroxide and with water and concentrated. The residue is triturated at −20° C. with acetonitrile and separated, affording a product with a melting point of 66° C.; $\overline{M}_n$: 3010.

EXAMPLE 18

(a) 14.8 g of the polymer obtained in Example 9(a) are suspended in 100 ml of n-butanol. Then triethylamine gas is introduced in the course of 6 hours and the mixture is allowed for stand for 16 hours. A sodium n-butanolate solution, prepared from 1 g of sodium and 50 ml of n-butanol, is then added dropwise. After stirring for 3 hours at room temperature, the mixture is concentrated and the residue is taken up in methylene chloride. The methylene chloride solution is washed with water, dried over anhydrous sodium sulfate and concentrated. The residue is triturated with acetonitrile, affording a product with a melting point of 179°–181° C.; $\overline{M}_n$: 5300.

(b) The above reaction is carried out with cyclohexanolate in cyclohexanol as solvent. Melting point: 194°–225° C.; $\overline{M}_n$: 3600.

EXAMPLE 19

(a) 12 g of the product obtained in Example 9(a) are dissolved in 30 ml of toluene and then 2.3 g of acetic anhydride are added to the solution. The mixture is allowed to stand for 2 days at room temperature, then diluted with toluene, washed with 2N sodium carbonate solution, dried and concentrated. The residue is treated with acetonitrile, affording 11 g of a colourless acetylation product. Melting point: 196°–207° C.; $\overline{M}_n$: 4300. This product contains about one acetyl group in each recurring structural unit.

(b) 11.1 g of undiluted acetic anhydride are boiled for 14 hours with 12 g of the starting material of (a). Excess anhydride is removed by distillation and the residue is worked up as described above. The resultant product has a melting point of 168°–192° C. and contains about 3 acetyl radicals in each recurring structural unit. $\overline{M}_n$: 4000.

EXAMPLE 20

(a) A solution of 14.8 g of the polymer obtained in Example 9(a) in 100 ml of toluene is saturated with trimethylamine gas and allowed to stand for 16 hours. With stirring, a solution of 1.95 g of potassium cyanide in 5 ml of water is added dropwise at room temperature and the mixture is allowed to react for 3 hours. The toluene phase is separated, washed with water and evaporated. The residue is triturated with acetonitrile and dried. The product melts at 200°–213° C. $\overline{M}_n$: 4300.

(b) A solution of 2.15 g of sodium azide in 5 ml of water is reacted in exactly the same way. The polymer azide melts at 181°–214° C. $\overline{M}_n$: 3800.

EXAMPLE 21

(a) 15 g of the polymer obtained in Example 9(a) is dissolved in 50 ml of toluene. With stirring, 6 g of benzoyl chloride and 85 ml of 1N sodium hydroxide solution are added to the above solution at 0°–5° C. The mixture is stirred for 14 hours at 0° C., then for 2 days at room temperature. The organic phase is separated, washed with 2N sodium hydroxide solution and with water, dried and concentrated. The residue is triturated with acetonitrile and filtered. Melting point of the product: 198°–210° C.; $\overline{M}_n$: 4300. The product contains about one benzoyl group in each recurring structural unit.

(b) The product obtained with n-hexylamine in Example 10 is benzoylated in the same manner. Melting point of the product: 179°–182° C.

EXAMPLE 22

A mixture of 12.1 g of 2-cyclohexylamino-4,6-dichlorotriazine, 57 g of 1,7-bis(2,2,6,6-tetramethyl-4-piperidyl)-1,4,7-triazaheptane, 4.0 g of finely powdered sodium hydroxide and 300 ml of toluene is stirred for 6 hours at 40° C. and then refluxed for 14 hours. The insoluble constituents are removed by filtration and the solvent is distilled off. The product is freed from unreacted starting material in a short way distillation apparatus. The residue melts at 64°–93° C.; $\overline{M}_n$: 1000.

EXAMPLE 23

10 g of the polymer obtained in Example 9(a) are dissolved in 90 ml of chloroform. With stirring, a solution of 3.7 g of cyanuric chloride in 10 ml of chloroform and 25 ml of 1N sodium hydroxide solution are added at 0°–5° C. The mixture is stirred at 0° C. until 0.02 mole of sodium hydroxide is consumed. The 5 g of n-butylamine are added and the mixture is reacted at 40° C. and then at 60° C. for 14 hours. The organic phase is separated, washed with 2N sodium hydroxide solution and with water, dried and concentrated. The product still contains one chlorine atom in each triazine ring. It can be reacted as described in Example 9(b) with amines to produce polymer triaminotriazines.

EXAMPLE 24

Light protective action in polypropylene filaments (130/137)

1000 parts of unstabilised polypropylene (melt index ∼15) are mixed in a high-speed mixer with 0.5 part of calcium (3,5-di-tert-butyl-4-hydroxybenzyl-monoethyl phosphonate), 1 part of calcium stearate and 3 parts of a stabiliser listed in the table below. The mixture is then extruded in an extruder at 220° C. and granulated. The granulate is spun to a 403/37 denier multifilament in a laboratory melt spinning machine at a maxiumum temperature of 270° C. and a speed of 600 m/minute. This multifilament is stretched and twisted on a draw twister. The stretch ratio is 1:3.2, such that finally multifilaments of 130/37 denier are obtained. These multifilaments are mounted on white cardboard and exposed in the xenotest 1200. The exposure time up to 50% loss in ultimate tensile strength is the criterion of the protective action. The results are reported in the table.

| Stabiliser | Exposure time up to 50% loss in ultimate tensile strength |
| --- | --- |
| compound of Ex. 4 (b) | 3500 h |
| compound of Ex. 4 (g) | 3400 h |
| compound without stabiliser | 420 h |

What is claimed is:

1. A polyamine of the formula

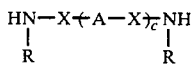

wherein X is $C_2$–$C_6$alkylene; A is —O—, —S— or —NR—; each R independently is hydrogen, $C_1$–$C_{23}$alkyl, $C_1$–$C_{23}$alkyl having oxygen in the alkyl chain, $C_3$–$C_{12}$cycloalkyl, $C_7$–$C_{18}$aralkyl, $C_6$–$C_{10}$aryl or the radical of the formula II

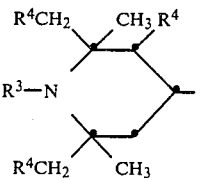

wherein $R^3$ is hydrogen, $C_1$–$C_{18}$alkyl, $C_3$–$C_{12}$alkenyl, $C_3$–$C_5$alkynyl, $C_3$–$C_{18}$alkoxyalkyl, $C_2$–$C_4$hydroxyalkyl, $C_2$–$C_4$hydroxyalkyl substituted by phenyl or phenoxy, or $C_7$–$C_{18}$aralkyl, and $R^4$ is hydrogen or methyl; c is an integer from 1 to 4; and wherein at least one R is a radical of the formula II.

2. The polyamine of claim 1, wherein c is 1 or 2.

* * * * *